United States Patent
Nagano et al.

(10) Patent No.: US 8,895,317 B2
(45) Date of Patent: Nov. 25, 2014

(54) REAGENT FOR MEASURING ACTIVE NITROGEN

(75) Inventors: Tetsuo Nagano, Tokyo (JP); Yasuteru Urano, Tokyo (JP); Saki Izumi, Tokyo (JP)

(73) Assignee: The University of Tokyo, Tokyo (JP)

(*) Notice: Subject to any disclaimer, the term of this patent is extended or adjusted under 35 U.S.C. 154(b) by 597 days.

(21) Appl. No.: 13/131,173

(22) PCT Filed: Dec. 4, 2009

(86) PCT No.: PCT/JP2009/006616
§ 371 (c)(1), (2), (4) Date: Aug. 11, 2011

(87) PCT Pub. No.: WO2010/064443
PCT Pub. Date: Jun. 10, 2010

(65) Prior Publication Data
US 2011/0287552 A1 Nov. 24, 2011

(30) Foreign Application Priority Data
Dec. 5, 2008 (JP) ................. 2008-311221

(51) Int. Cl.
*G01N 33/48* (2006.01)
*C07D 311/82* (2006.01)
*G01N 31/22* (2006.01)

(52) U.S. Cl.
CPC .................... *G01N 31/22* (2013.01)
USPC ........... 436/110; 436/107; 436/116; 436/117; 436/118; 436/172; 549/223

(58) Field of Classification Search
USPC .......... 436/107, 110, 116–118, 172; 549/223
See application file for complete search history.

(56) References Cited

U.S. PATENT DOCUMENTS 2,745,720 A * 5/1956 Schwarzenbach et al. ..... 436/73
3,301,870 A * 1/1967 Terzijska et al. ............. 548/524
(Continued)

FOREIGN PATENT DOCUMENTS

JP 9-43153 A 2/1997
JP 10-226688 A 8/1998
(Continued)

OTHER PUBLICATIONS

Kojima, H. et al, Analytical Chemistry 1998, 70, 2446-2453.*
(Continued)

*Primary Examiner* — Arlen Soderquist
(74) *Attorney, Agent, or Firm* — Greenblum & Bernstein, P.L.C.

(57) ABSTRACT

A compound represented by the general formula (I) [$R^1$ and $R^2$ are amino groups that substitute at adjacent positions on the benzene ring; $R^3$ and $R^4$ are halogen atoms; $R^5$ and $R^6$ represent hydrogen atom, an acyl group or an acyloxy($C_{1-6}$ alkyl) group; $R^7$ and $R^8$ represent —$(CH_2)_p$—$N(R^9)(R^{10})$ (p is 1 to 4, and $R^9$ and $R^{10}$ represent —$(CH_2)_n$—COOH (n is 1 to 4))], which is useful for measuring a reactive nitrogen species existing in cells such as nitrogen monoxide or peroxynitrite at high sensitivity over a long period of time.

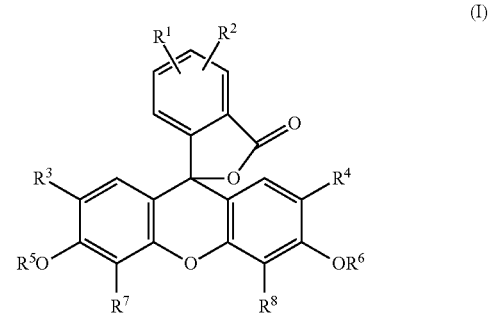

6 Claims, 4 Drawing Sheets

(56) References Cited

U.S. PATENT DOCUMENTS

| | | | |
|---|---|---|---|
| 5,874,590 A * | 2/1999 | Nagano et al. | 549/223 |
| 6,162,931 A * | 12/2000 | Gee et al. | 549/223 |
| 6,441,197 B1 * | 8/2002 | Nagano et al. | 549/224 |
| 6,569,892 B2 * | 5/2003 | Nagano et al. | 514/455 |
| 6,833,386 B2 * | 12/2004 | Nagano et al. | 514/453 |
| RE40,572 E * | 11/2008 | Nagano et al. | 549/391 |
| 7,618,997 B2 * | 11/2009 | Nagano et al. | 514/455 |
| 8,410,164 B2 | 4/2013 | Nagano | |
| 2002/0137225 A1 * | 9/2002 | Nagano et al. | 436/116 |
| 2003/0171600 A1 * | 9/2003 | Nagano et al. | 549/225 |
| 2005/0123478 A1 | 6/2005 | Nagano et al. | |
| 2005/0130314 A1 * | 6/2005 | Nagano et al. | 436/116 |
| 2006/0211122 A1 * | 9/2006 | Nagano et al. | 436/110 |
| 2007/0117211 A1 * | 5/2007 | Nagano et al. | 436/116 |
| 2008/0281104 A1 | 11/2008 | Nagano et al. | |
| 2011/0111515 A1 | 5/2011 | Nagano et al. | |
| 2011/0251404 A1 | 10/2011 | Nagano | |

FOREIGN PATENT DOCUMENTS

| | | |
|---|---|---|
| JP | 2003-130797 A | 5/2003 |
| JP | 2003-277385 A | 10/2003 |
| WO | 02/18362 A1 | 3/2002 |
| WO | 2006/093252 A1 | 9/2006 |

OTHER PUBLICATIONS

Keller, A. et al, Free Radical Research 2004, 38, 1257-1267.*

Bartosz, G., Clinica Chimica Acta 2006, 368, 53-76.*

Lepiller, S. et al, Free Radical Biology & Medicine 2007, 43, 619-627.*

Bermejo-Martinez, F. et al, Analytica Chimica Acta 1969, 47, 139-144.*

Zuo, L. et al, Methods in Enzymology 2002, 352, 307-25.*

Mokhir, A. et al, Inorganic Chemistry 2005, 44, 5661-5666.*

Jang, Y. J. et al, Journal of Organic Chemistry 2005, 70, 9603-9606.*

LeBel, C. P. et al, Chemical Research in Toxicology 1992, 5, 227-231.*

Crow, J. P., Nitric Oxide: Biology and Chemistry 1997, 1, 145-157.*

Kooy, N. W. et al, Free Radical Research 1997, 27, 245-254.*

Nagano, T. et al, Chemical Reviews 2002, 102, 1235-1269.*

Jourd'Heuil, D., Free Radical Biology Biology and Medicine 2002, 33, 676-684.*

Gledska, J. et al, Free Radical Biology and Medicine 2003, 35, 676-682.*

Gomes, A. et al, Journal of Fluorescence 2006, 16, 119-139.*

Wardman, P., Free Radical Biology and Medicine 2007, 43, 995-1022.*

Saki Izumi et al., "Saibonai Tairyusei o Kaizen Shita, Shinki hROS Kenshutsu Keiko Probe no Kaihatsu", Symposium on Biomedical-Analytical Sciences, vol. 21. (2008)., Aug. 1, 2008, pp. 35-36.

Saki Izumi et al., "A Simple and Effective Strategy to Increase the Sensitivity of Fluorescence Probes in Living Cells", Journal American Chemical Society, vol. 131, No. 29, (2009). "JACS" Articles, Jul. 2, 2009, pp. 10189-10200.

U.S. Appl. No. 12/991,750 to Tetsuo Nagano et al., filed Nov. 9, 2010.

* cited by examiner

REAGENT FOR MEASURING ACTIVE NITROGEN

TECHNICAL FIELD

The present invention relates to a compound that enables measurement of reactive nitrogen species existing in cells such as nitrogen monoxide or peroxynitrite at high sensitivity over a long period of time, and a reagent for the measurement comprising said compound.

BACKGROUND ART

Nitrogen monoxide (NO) is an unstable radical having a short life. It has been elucidated that nitrogen monoxide has important functions as a physiologically active substance in vivo (special topics in Gendai Kagaku (Chemistry Today), April, 1994). Methods for measuring nitrogen monoxide are mainly classified into indirect methods where oxidative degradation products of nitrogen monoxide such as $NO_2$. or $NO_3$. are measured, and methods where nitrogen monoxide is directly measured. The direct methods have been focused from the standpoint that they achieve detection and quantification of nitrogen monoxide under physiological conditions. However, no measuring method has been developed to date that has sufficient specificity and high sensitivity and is applicable to an in vitro system.

For example, a chemiluminescence method which utilizes luminescence emitted during ozone oxidation of NO radicals (Palmer, R. M., et al., Nature, 327, pp. 524-526, 1987); a method which comprises the step of measuring an absorption spectrum of metHb that is produced by oxidation of oxyhemoglobin ($O_2$Hb) (Kelm, M., et al., Circ. Res., 66, pp. 1561-1575, 1990); a method which comprises the step of measuring electric current generated during oxidation by means of electrodes that are inserted into a tissue (Shibuki, K., Neurosci. Res., 9, pp. 69-76, 1990; Malinski, T., Nature, 356, pp. 676-678, 1992); the Griess reaction method (Green, L. C., et al., Anal. Biochem., 126, pp. 131-138, 1992) and the like are known as typical methods (as reviews, see, "3. Method for measuring NO," by Tetsuo Nagano, pp. 42-52, in "Approach from the Latest Medicine 12, NO" edited by Noboru Toda, published by Medical View Co., Ltd.; and Archer, S., FASEB J., 7, pp. 349-360, 1993).

The Griess reaction method comprises a detection step that utilizes azo coupling between naphthylethylenediamine and a diazonium salt compound formed with $NO_2$. which is generated by the oxidation of nitrogen monoxide radicals. This method is advantageous because it does not require particular apparatuses or techniques, although nitrogen monoxide radicals are not directly measured by the method. In addition, $NO_3$. can also be measured after being reduced to $NO_2$. by using cadmium (Stainton, M. P., Anal. Chem., 46, p. 1616, 1974; Green, L. C., et al., Anal. Biochem., 126, pp. 131-138, 1982) or hydrazine (Sawicki, C. R. and Scaringelli, F. P., Microchem. J., 16, pp. 657-672, 1971), and accordingly, the method also has a characteristic feature that it enables the measurement of metabolites related to nitrogen monoxide.

As well as the Griess reaction method, 2,3-Diaminonaphthalene as a reagent has also been known for measuring nitrogen monoxide by detecting $NO_2$. This reagent reacts with $NO_2$. under an acidic condition to form a fluorescent adduct, i.e., naphthalenetriazole (chemical name: 1-[H]-naphtho[2,3-d]triazole) (Wiersma, J. H., Anal. Lett., 3, pp. 123-132, 1970). Details of the reaction conditions of 2,3-diaminonaphthalene and $NO_2$. have been studied, and it has been found that the reaction proceeds most rapidly at a pH not higher than 2, and completes in about 5 minutes at room temperature (Wiersma, J. H., Anal. Lett., 3, pp. 123-132, 1970; Sawicki, C. R., Anal. Lett., 4, pp. 761-775, 1971). The resulting adduct emits fluorescence most efficiently at a pH not lower than 10 (Damiani, P. and Burini, G., Talanta, 8, pp. 649-652, 1986).

The method for measuring nitrogen monoxide using the above 2,3-diaminonaphthalene has characteristic features of 50- to 100-fold higher sensitivity compared with the Griess reaction method, since its detection limit is as low as approximately several tens nM (Misko, T. P., Anal. Biochem. 214, pp. 11-16, 1993). This method is highly advantageous because it needs no particular apparatus or technique and can be carried out conveniently (as a review of the aforementioned method, see, DOJIN News. No. 74, Information, "Reagent for the determination of NO: 2,3-diaminonaphthalene," Dojindo Laboratories Inc., 1995). However, the method does not utilize nitrogen monoxide, per se, but utilizes an oxidation product thereof, i.e., $NO_2$., as a reactant. Accordingly, the method is considered as an indirect method in contrast to the method of directly measuring nitrogen monoxide. Furthermore, because the reaction of 2,3-diaminonaphthalene with $NO_2$. is carried out under a strongly acidic condition (pH not higher than 2), the method has a problem that it cannot be employed for detection or quantification of nitrogen monoxide under a physiological condition.

The inventors of the present invention conducted researches to provide a means that enables direct and highly sensitive measurement of nitrogen monoxide under a physiological condition, and as a result, they found that nitrogen monoxide efficiently reacted with 2,3-diaminonaphthalene or its derivatives, even under a neutral condition, in the presence of an oxygen source such as dissolved oxygen or oxide compounds (e.g., PTIO and derivatives thereof such as carboxy-PTIO), to give a fluorescent naphthalenetriazole or a derivative thereof. They also found that a method for measuring nitrogen monoxide utilizing the above reaction was excellent in high detection sensitivity, and achieved accurate quantification of a very small amount of nitrogen monoxide (see, the specification of Japanese Patent Application No. Hei 7 (1995)-189978).

However, the aforementioned method utilizing 2,3-diaminonaphthalene requires irradiation of excitation light having a short wavelength of approximately 370 to 390 nm for the detection of fluorescence, and this may cause damages to cells and/or tissues in a measurement system. Strong autofluorescence of cells, per se, may also possibly affect the measurement, and moreover, there is a problem that a fluorescence filter provided on a usual fluorescence microscope fails to sufficiently cut off excitation light during the fluorescence measurement. In addition, the fluorescent triazole compound formed from 2,3-diaminonaphthalene does not always have a sufficient fluorescence intensity, and therefore, it is difficult to achieve accurate measurement of intracellular fluorescence of an individual cell by ordinary fluorescence microscopy. In addition, since 2,3-diaminonaphthalene itself has a simple chemical structure, there is another problem that the compound is not suitable as a fundamental structure for various chemical modifications so as to achieve intracellular localization of the reagent.

As a method for quantifying nitrogen monoxide that solved these problems, the inventors of the present invention proposed a method utilizing a class of diaminofluorescein derivatives (U.S. Pat. No. 5,874,590). By using these derivatives, nitrogen monoxide can be measured with an excitation light of a long wavelength that gives no damage to living tissues or cells, and intracellularly existing nitrogen monoxide can be accurately measured for each individual cell. However, these diaminofluorescein derivatives are not satisfactory reagents from a standpoint of intracellular retentivity, and quickly leak from the inside of cells, and therefore it is difficult to measure nitrogen monoxide over a long period of time.

PRIOR ART REFERENCE

Patent document

Patent document 1: U.S. Pat. No. 5,874,590

SUMMARY OF THE INVENTION

Object to be Achieved by the Invention

An object of the present invention is to provide a reagent for measuring reactive nitrogen species existing in cells such as nitrogen monoxide or peroxynitrite at high sensitivity over a long period of time.

Means for Achieving the Object

The inventors of the present invention made efforts to achieve the foregoing object, and as a result, they found that diaminofluorescein derivatives in which two alkyl groups, each having an amino group substituted with two carboxyalkyl groups, were introduced into the xanthene structure had extremely superior intracellular retentivity and high reactivity with reactive nitrogen species. They also found that reactive nitrogen species existing in individual cells was accurately and conveniently measurable over a long period of time by using these compounds as a reagent for measuring nitrogen monoxide. The present invention was achieved on the basis of these findings.

The present invention thus provides a compound represented by the following general formula (I);

[Formula 1]

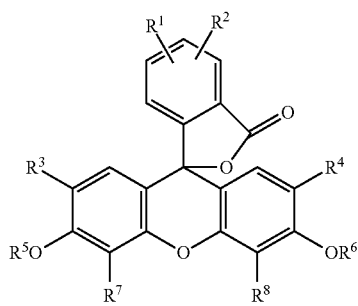

(I)

wherein $R^1$ and $R^2$ represent amino groups that substitute at adjacent positions on the benzene ring, provided that either one of $R^1$ and $R^2$ represents a mono($C_{1-6}$ substituted amino group or unsubstituted amino group, and the other represents unsubstituted amino group; $R^3$ and $R^4$ independently represent a halogen atom; $R^5$ and $R^6$ independently represent hydrogen atom, an acyl group or an acyloxy($C_{1-6}$ alkyl) group; and $R^7$ and $R^8$ independently represent a group represented by —$(CH_2)_p$—$N(R^9)(R^{10})$ (in the formula, p represents an integer of 1 to 4, and $R^9$ and $R^{10}$ independently represent a group represented as —$(CH_2)_n$—COOH wherein n represents an integer of 1 to 4), a salt thereof, or an ester thereof.

According to a preferred embodiment of the aforementioned invention, there is provided the aforementioned compound wherein $R^1$ and $R^2$ are unsubstituted amino groups that substitute at adjacent positions on the benzene ring, $R^3$ and $R^4$ are chlorine atoms, $R^5$ and $R^6$ independently represent hydrogen atom or acetoxymethyl group, and $R^7$ and $R^8$ are groups represented as —$CH_2$—$N(CH_2$—$COOH)_2$, a salt thereof, or an ester thereof.

According to another aspect of the present invention, there is provided a reagent for measuring a reactive nitrogen species, preferably nitrogen monoxide, which comprises a compound represented by the aforementioned general formula (I), a salt thereof, or an ester thereof.

According to still another aspect of the present invention, there is provided a compound represented by the following general formula (II):

[Formula 2]

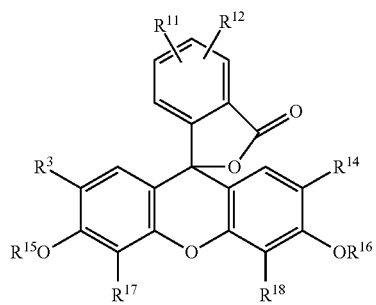

(II)

wherein $R^{11}$ and $R^{12}$ combine together to form a group represented as —N=N—N($R^{19}$)— which forms a ring structure at adjacent positions on the benzene ring (in the formula, $R^{19}$ represents hydrogen atom or a $C_{1-6}$ alkyl group); $R^{13}$ and $R^{14}$ independently represent a halogen atom; $R^{15}$ and $R^{16}$ independently represent hydrogen atom, an acyl group or an acyloxy($C_{1-6}$ alkyl) group; $R^{17}$ and $R^{18}$ independently represent a group represented as —$(CH_2)_s$—$N(R^{19})(R^{20})$ (in the formula, s represents an integer of 1 to 4, and $R^{19}$ and $R^{20}$ independently represent a group represented by —$(CH_2)_t$—COOH wherein t represents an integer of 1 to 4), a salt thereof, or an ester thereof.

The present invention also provides a method for measuring a reactive nitrogen species, preferably nitrogen monoxide, which comprises:

(1) the step of reacting a compound represented by the aforementioned general formula (I), a salt thereof, or an ester thereof with a reactive nitrogen species, preferably nitrogen monoxide; and (2) the step of detecting a compound represented by the aforementioned general formula (II), a salt thereof, or an ester thereof formed in the above step (1).

MODES FOR CARRYING OUT THE INVENTION

Figure 1:
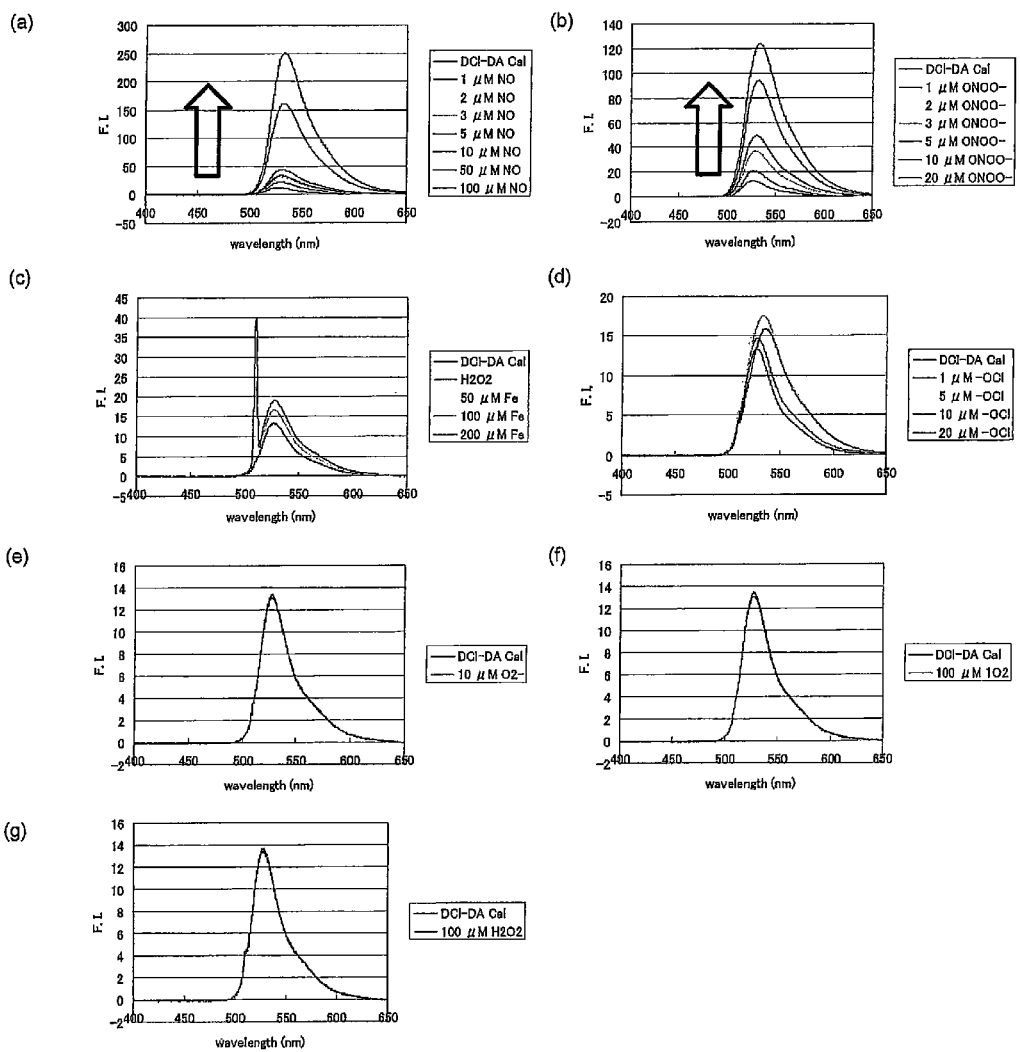
FIG. 1 shows results of reactions of DAI-DA Cal with reactive oxygen species or reactive nitrogen species, including results of reactions with (a) nitrogen monoxide; (b) peroxynitrite; (c) hydroxyl radical; (d) hypochlorous acid; (e) superoxide; (f) singlet oxygen; and (g) hydrogen peroxide.

In the above general formula (I), $R^1$ and $R^2$ represent amino groups which substitute at adjacent positions on the benzene ring. Either one of $R^1$ and $R^2$ represents a mono($C_{1-6}$ alkyl)-substituted amino group or unsubstituted amino group, and the other represents unsubstituted amino group. The $C_{1-6}$ alkyl group constituting the mono($C_{1-6}$ alkyl)-substituted amino group may be straight or branched. More specifically, methyl group, ethyl group, n-propyl group, isopropyl group, n-butyl group, sec-butyl group, tert-butyl group and the like may be used. Other $C_{1-6}$ alkyl groups or $C_{1-6}$ alkyl moieties in functional groups containing a $C_{1-6}$ alkyl moiety, which are referred to in the specification, may be similar to those explained above. It is preferred that both $R^1$ and $R^2$ are unsubstituted amino groups. The substitution positions of $R^1$ and $R^2$ are preferably ortho position and meta position relative to the carbonyl group constituting the lactone ring.

$R^3$ and $R^4$ independently represent a halogen atom. As the halogen atom, fluorine atom, chlorine atom, bromine atom, or iodine atom can be used, and fluorine atom or chlorine atom is preferred. It is particularly preferred that both $R^3$ and $R^4$ are chlorine atoms.

$R^5$ and $R^6$ independently represent hydrogen atom, an acyl group, or an acyloxy($C_{1-6}$ alkyl) group. As the acyl group, for example, an arylcarbonyl group such as benzoyl group, p-methoxybenzoyl group, p-chlorobenzoyl group, or naphthylcarbonyl group; a ($C_{1-6}$ alkyl)carbonyl group such as acetyl group, propionyl group, or butanoyl group and the like can be used. As the acyl moiety of the acyloxy($C_{1-6}$ alkyl) group, the aforementioned acyl group can be used. As the acyloxy($C_{1-6}$ alkyl) group, for example, an acetoxy($C_{1-6}$ alkyl) group and the like are preferred, and acetoxymethyl group and the like can be more preferably used. It is preferred that $R^5$ and $R^6$ independently represent hydrogen atom or an acyloxy($C_{1-6}$ alkyl) group, and it is particularly preferred that both $R^5$ and $R^6$ are hydrogen atoms, or methoxymethyl groups.

$R^7$ and $R^8$ may be the same or different, and they independently represent —$(CH_2)_p$—$N(R^9)(R^{10})$. Symbol p represents an integer of 1 to 4, $R^9$ and $R^{10}$ independently represent —$(CH_2)_n$—COOH, and n represents an integer of 1 to 4. When $R^7$ and $R^8$ are different, p and/or n may represent different integers. $R^7$ and $R^8$ are preferably the same, and p is preferably an integer of 1 to 3, more preferably 1 or 2, particularly preferably 1. In $R^9$ and $R^{10}$, n is preferably an integer of 1 to 3, more preferably 1 or 2, particularly preferably 1. It is particularly preferred that both $R^7$ and $R^8$ are —$CH_2$—N($CH_2$—COOH)$_2$.

Among the compounds represented by the aforementioned general formula (I), preferred compound includes a compound wherein $R^1$ and $R^2$ are unsubstituted amino groups that substitute at adjacent positions on the benzene ring, $R^3$ and $R^4$ are chlorine atoms, $R^5$ and $R^6$ independently represent hydrogen atom or acetoxymethyl group, and $R^7$ and $R^8$ are the groups represented as —$CH_2$—N($CH_2$—COOH)$_2$, and particularly preferred compound includes a compound wherein $R^1$ and $R^2$ are unsubstituted amino groups that substitute at adjacent positions on the benzene ring, $R^3$ and $R^4$ are chlorine atoms, $R^5$ and $R^6$ are hydrogen atoms, and $R^7$ and $R^8$ are groups represented as —$CH_2$—N($CH_2$—COOH)$_2$.

In the aforementioned general formula (II), $R^{11}$ and $R^{12}$ combine together to form a group represented as —N=N—N($R^{19}$) which forms a ring structure at adjacent positions on the benzene ring, and $R^{19}$ represents hydrogen atom or a $C_{1-6}$ alkyl group.

In the aforementioned general formula (II), $R^{13}$ and $R^{14}$ correspond to $R^3$ and $R^4$ in the aforementioned general formula (I), respectively, $R^{15}$ and $R^{16}$ correspond to $R^5$ and $R^6$ in the aforementioned general formula (I), respectively, and $R^{17}$ and $R^{18}$ correspond to $R^7$ and $R^8$ in the aforementioned general formula (I), respectively. Specific examples and preferred range of those groups are the same as those explained for the aforementioned general formula (I).

The compound represented by the aforementioned general formula (I) or (II) may exist as a salt. Examples of the salt include a base addition salt, an acid addition salt, an amino acid salt, and the like. Examples of the base addition salt include, for example, metal salts such as sodium salts, potassium salts, calcium salts, and magnesium salts; ammonium salts; and organic amine salts such as triethylamine salts, piperidine salts, and morpholine salts. Examples of the acid addition salt include, for example, mineral acid salts such as hydrochlorides, sulfates, and nitrates; and organic acid salts such as methanesulfonates, p-toluenesulfonates, citrates, and oxalates. Examples of the amino acid salt include glycine salts and the like. However, salts of the compounds of the present invention are not limited to these examples. Among them, physiologically acceptable water-soluble salts can be preferably used for the reagent and the measurement method of the present invention.

As the ester of the compound represented by the aforementioned general formula (I) or (II), physiologically acceptable esters are preferred. Preferred examples of ester residue include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutyryloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy) ethyl group, ethoxycarbonyloxymethyl group, 1-(ethoxycarbonyloxy)ethyl group, prop oxycarbonyloxymethyl group, 1-(propoxycarbonyloxy)ethyl group, isopropoxycarbonyloxymethyl group, 1-(isopropoxycarbonyloxy) ethyl group, butoxycarbonyloxymethyl group, 1-(butoxycarbonyloxy)ethyl group, isobutoxycarbonyloxymethyl group, 1-(isobutoxycarbonyloxy)ethyl group, t-butoxycarbonyloxymethyl group, 1-(t-butoxycarbonyloxy) ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopentyloxycarbonyloxymethyl group, 1-(cyclopentyloxycarbonyloxy)ethyl group, cyclohexyloxycarbonyloxymethyl group, (cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like, but the examples are not limited to these. As for the ester, it is preferred that four carboxyl groups of $R^7$ and $R^8$ form esters, and it is more preferred that these esters are the same esters. The carboxyl group of the carboxyphenyl group in the fluorescein structure may form an ester as the case may be.

The compound represented by the general formula (I) or (II) in free form, a salt thereof, or an ester thereof may exist as a hydrate or a solvate, and all of these substances fall within the scope of the present invention. The type of solvent that forms the solvate is not particularly limited. The solvents can be exemplified by ethanol, acetone and isopropanol.

The compound represented by the general formula (I) or (II) may have one or more asymmetric carbons depending on the type of the substituent, and stereoisomers such as optical isomers or diastereoisomers may exist. These stereoisomers in pure forms, arbitrary mixtures of these stereoisomers, racemates and the like all fall within the scope of the present invention. Optical isomers based on the lactone formation are also fall within the scope of the present invention.

It is known that fluorescein derivatives may also exist as compounds in which the lactone ring is not formed [9-(o-carboxyphenyl)-6-hydroxy-3H-xanthen-3-one]. It is readily understood by those skilled in the art that the compounds of the present invention represented by the general formulas (I) and (II) can also exist in such a form that the lactone ring is cleaved to form 2-carboxyphenyl group, and such compounds in which the lactone ring is cleaved are tautomers of the compounds represented by the aforementioned general formulas (I) and (II) having the lactone ring. Therefore, it should be noted that the compounds in which the lactone ring is cleaved fall within the scope of the present invention. The aforementioned general formulas (I) and (II) are depicted, for convenience, so as to include only the compounds in which the lactone ring is formed, whereas in the synthesis schemes described in this specification, only one of the tautomers may be indicated also for convenience.

The compounds represented by the aforementioned general formula (I) can be readily prepared by, for example, introducing groups corresponding to $R^7$ and $R^8$ (these may be protected) into a fluorescein derivative having adjacent amino group and nitro group on the benzene ring used as a starting compound, and then reducing the nitro group. The aforementioned nitro compound can be prepared by, for example, the method described in U.S. Pat. No. 5,874,590. The preparation methods for typical compounds among the compounds of the present invention represented by the general formula (I) are specifically described in the examples mentioned in this specification, and accordingly, those skilled in the art can readily prepare the compounds of the present invention by appropriately choosing starting materials and reaction reagents on the basis of the specific explanations of the examples, and appropriately altering or modifying the reaction conditions or the reaction steps, if needed. The compounds represented by the general formula (II) can be easily produced by, for example, reacting nitrogen monoxide with a compound represented by the general formula (I).

A target compound may be efficiently prepared by performing the reaction with optionally protecting a particular class of functional group in the reaction steps. Detailed explanations of protective groups are given in, for example, Protective Groups in Organic Synthesis, T. W. Greene, John Wiley & Sons, Inc., 1981, and the like, and one of ordinary skill in the art can choose suitable protective groups.

In the above preparation methods, isolation and purification of the products can be performed by an appropriate combination of techniques used in ordinary organic synthesis, for example, filtration, extraction, washing, drying, concentration, crystallization, various chromatography techniques and the like. The synthetic intermediates in the aforementioned steps can also be used for the subsequent reaction without particular purification. Where a salt of the compound of the present invention is prepared, when a salt of each compound is obtained in the above preparation method, the resulting salt, per se, may be purified, and when a compound in a free form is obtained, the compound in a free form can be dissolved or suspended in a suitable solvent and then with a base is added thereto to form a salt, and the resulting salt may be purified, if necessary.

The compounds represented by the aforementioned general formula (I) have a property that they efficiently react with a reactive nitrogen species (RNS) to generate a compound of the general formula (II) in an excellent yield. The compounds represented by the general formula (I), per se, emit almost no fluorescence when they are irradiated with an excitation light of about 500 nm under a neutral condition, whereas the compounds of the aforementioned formula (II) have a property that they emit strong fluorescence (emission: 520 nm) under the same condition. Therefore, by allowing a compound represented by the general formula (I) to be taken up into a biological tissue or cell and react with a reactive nitrogen species to generate the fluorescent compound represented by the aforementioned general formula (II), and measuring fluorescence of this compound, the reactive nitrogen species in the biological tissue or cell can be measured.

Examples of the reactive nitrogen species include, for example, nitrogen monoxide, peroxynitrite, and the like, and nitrogen monoxide is a preferred measurement object. In this specification, the term "measurement" should be construed in its broadest sense, including measurements for various purposes, such as detection, quantification, and qualification. The aforementioned reaction can be preferably performed under a neutral condition, for example, in the range of pH 6.0 to 8.0, preferably in the range of pH 6.5 to 7.8, more preferably in the range of pH 6.8 to 7.6. However, the measurement of nitrogen monoxide using the compound of the present invention is not limited to a method performed in a neutral range or a weakly acidic range.

The compounds of the present invention represented by the general formulas (I) and (II) can be easily taken up into cells and retained over a long period of time without leaking out of the cells. Accordingly, the compounds have a superior property that they enables detection of reactive nitrogen species in cells over a long period of time. In particular, the compounds of the present invention represented by the general formula (II) have a property that they emit extremely strong fluorescence, and show superior intracellular retentivity, and therefore they have a characteristic feature that they enable measurement of a very small amount of a reactive nitrogen species existing in cells with high sensitivity over a long period of time. Esters of the compounds represented by general formula (I) are highly liposoluble, and have a property that they can easily pass through liposoluble cell membranes and can be efficiently taken up into cells, and after the uptake, they can be hydrolyzed in the cells to generate a corresponding compound having carboxyl group.

Although the compounds represented by aforementioned formula (I) or a salt thereof may be used per se as a reagent for measuring reactive nitrogen of the present invention, they may be used as a composition by mixing with additives generally used for reagent preparation, if necessary. For example, as additives for use of the reagent under a physiological condition, additives such as dissolving aids, pH adjusters, buffers, isotonic agents and the like can be used, and amounts of these additives can suitably be chosen by those skilled in the art. Such a composition may be provided as in an appropriate form, for example, powdery mixtures, lyophilized products, granules, tablets, solutions and the like.

EXAMPLES

Hereafter, the present invention will be more specifically explained with reference to examples. However, the scope of the present invention is not limited to the following examples.

Example 1

[Formula 3]

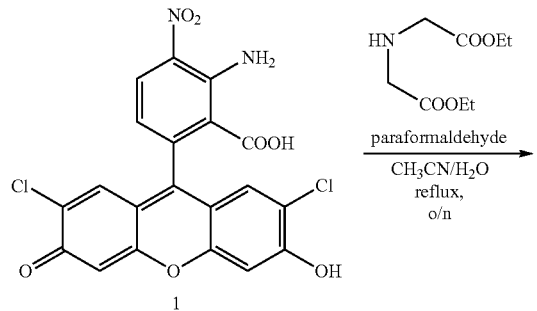

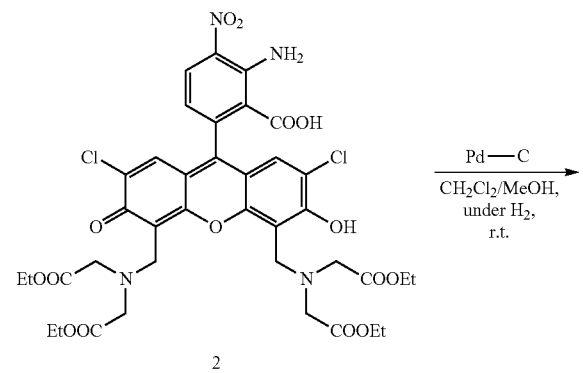

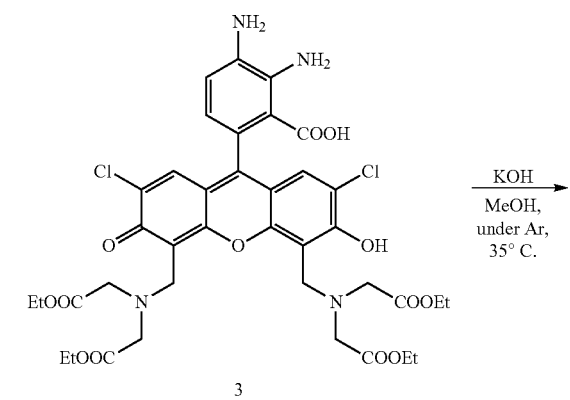

4
(DCl-DA Cal)

3-Amino-4-nitrofluorescein (Compound 1, 29 mg), diethyl iminodiacetate (37 mg) and paraformaldehyde (40.7 mg) were suspended in a mixed solution of acetonitrile (3.5 ml) and water (1.5 ml), and the suspension was refluxed by heating for 24 hours. The reaction mixture was left to cool to room temperature, and then the solvent was evaporated under reduced pressure to obtain Compound 2.

Compound 2 was dissolved in 10 ml of a mixed solvent of dichloromethane and methanol (9:1), to the solution was added 36 mg of 10% Pd—C, and the mixture was stirred for 5 minutes under a hydrogen atmosphere. After the catalyst was removed by filtration, the solvent was evaporated under reduced pressure to obtain Compound 3.

Compound 3 was dissolved in a 1 N solution of potassium hydroxide in methanol, and the solution was stirred at 35° C. for 3 hours. After the reaction mixture was neutralized with 2 N hydrochloric acid, the solvent was evaporated under reduced pressure, and the residue was purified by HPLC to obtain Compound 4 (DCl-DA Cal) as yellow powder (22.8 mg, yield: 50% for the three steps).

$^1$H-NMR (300 MHz, CD$_3$OD) δ 3.78 (s, 8H), 4.52 (s, 4H), 6.23 (d, 1H, J=7.32), 6.73 (s, 2H), 7.09 (d, 1H, J=8.07)

$^{18}$C-NMR (100 MHz, CDCl$_3$) δ 42.3, 49.5, 55.3, 83.0, 110.4, 110.5, 112.2, 113.4, 116.2, 118.5, 119.1, 129.9, 150.3, 156.4, 161.8, 162.1, 171.6, 172.3

HRMS (ESI+) m/z Calcd for [M+H]+721.09517, Found, 721.09928 (4.12 mmu)

Example 2

[Formula 4]

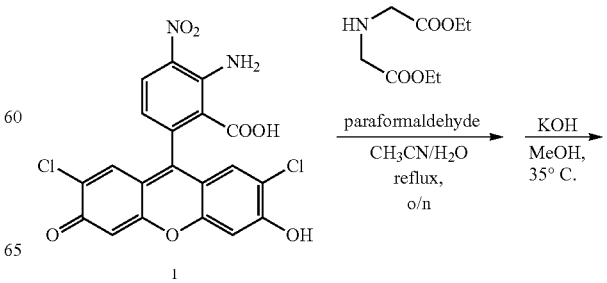

-continued

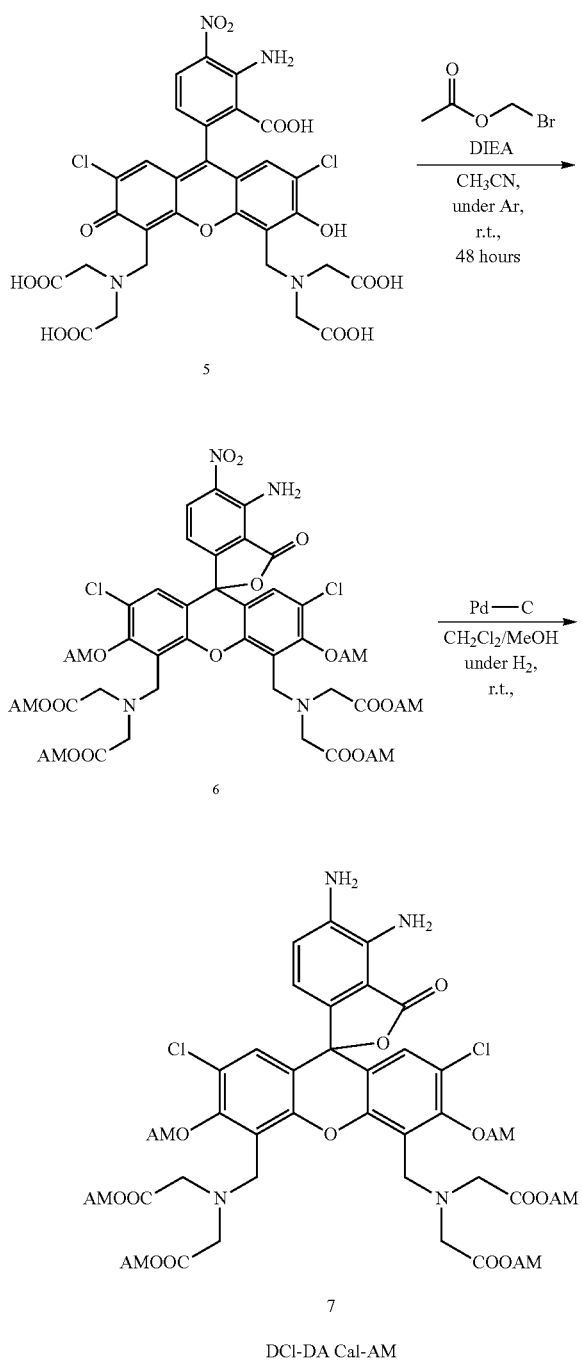

DCl-DA Cal-AM

Compound 1 (100 mg), diethyl iminodiacetate (130 mg), and paraformaldehyde (56.6 mg) were suspended to in a mixed solution of acetonitrile (3.5 ml) and water (1.5 ml), and the suspension was refluxed by heating for 24 hours. After the reaction mixture was left to cool to room temperature, the solvent was evaporated under reduced pressure. The residue was dissolved in a 1 N solution of potassium hydroxide in methanol, and the solution was stirred at 35° C. for 3 hours. After the reaction mixture was neutralized with 2 N hydrochloric acid, the solvent was evaporated under reduced pressure. The residue was purified by HPLC to obtain Compound 5 as yellow powder (131.2 mg, yield: 81% for the two steps).

Compound 5 (51.2 mg) was dissolved in acetonitrile, to the solution was added diisopropylethylamine (DIEA, 352.5 mg) and bromomethyl acetate (421.2 mg), and the mixture was stirred for 48 hours under an argon atmosphere. After the reaction mixture was neutralized with acetic acid, the solvent was evaporated under reduced pressure, and the residue was purified by HPLC to obtain Compound 6 as pale yellow powder (15.4 mg).

Compound 6 (15 mg) was dissolved in 3 ml of a mixed solvent of dichloromethane and methanol (1:1), and to the solution was added 220 mg of 10% Pd—C to perform catalytic reduction under a hydrogen atmosphere. After completion of the reaction, the catalyst was removed by filtration, and the solvent was evaporated under reduced pressure. The residue purified by HPLC to obtain Compound 7 (DCl-DA Cal-AM, 4.9 mg, yield: 33.4%) as pale yellow powder.

$^1$H-NMR (300 MHz, CDCl$_3$) δ 2.08 (s, 12H), 2.17 (s, 6H), 3.75 (s, 8H), 4.34 (m, 4H), 6.70 (s, 8H), 5.78 (s, 4H), 6.49 (d, 211, J=8.07), 6.94 (s, 2H) 8.50 (d, 11-1, J=8.79)

HRMS (ESI+) m/z Calcd for [M+Na]+1205.17807, Found, 1205.17779 (−0.28 mmu)

Example 3

Reactivity of DCl-DA Cal with reactive oxygen species (ROS) and reactive nitrogen species (RNS) was examined. The fluorescence spectra of DCl-DA Cal observed after addition of reactive oxygen species and reactive nitrogen species are shown in FIG. 1. When reactive nitrogen species such as peroxynitrite and nitrogen monoxide were added, DCl-DA Cal showed significant increase of fluorescence in a concentration dependent manner ((a) and (b) in FIG. 1), but when reactive oxygen species were added, the compound did not show significant increase of fluorescence. These results showed that DCl-DA Cal was a fluorescent probe enabling specific detection of reactive nitrogen species.

DCl-DA Cal is a substantially non-fluorescent substance ($\Phi_f$=0.013), and specifically reacts with a reactive nitrogen species to give a triazole compound, and this triazole compound shows extremely high fluorescence intensity at a physiological pH ($\Phi_f$=0.63), and is stable under physiological conditions. Moreover, this triazole compound shows extremely superior intracellular retentivity. Therefore, use of DCl-DA Cal enables observation of intracellular reactive nitrogen species over such a long period of time that cannot be achieved by conventional fluorescent probes for measuring reactive nitrogen.

It was confirmed by $^1$H-NMR and HRMS that the fluorescent substance generated by the addition of the reactive nitrogen species was a triazole compound (DCl-triazole calcein).

$^1$H-NMR (300 MHz, CD$_3$OD) δ 3.76 (s, 8H), 4.53 (s, 4H), 6.78 (s, 2H), 7.19 (d, 1H, J=8.79), 8.31 (d, 1H, J=8.79)

HRMS (ESI+) Calcd for [M−H]−730.05912, Found, 730.05731 (−1.80 mmu)

[Formula 5]

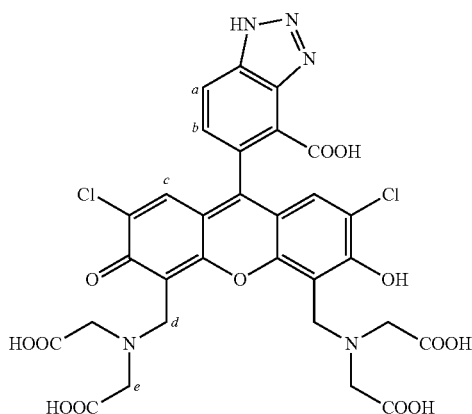

Example 4

Nitrogen monoxide was added to HeLa cells from the outside of the cells, and nitrogen monoxide in the cells was measured. DCl-DA Cal-AM having superior cell membrane permeability was used as the compound of the present invention. After uptake into cells, this compound gives DCl-DA Cal through hydrolysis of the ester, and this DCl-DA Cal reacts with nitrogen monoxide to give the aforementioned triazole compound. As a comparative compound, a conventional reagent for measuring nitrogen monoxide, DAF2-DA (Kojima H. et al., J. Biol. Chem., 2003, 278, 31703175), was used.

Figure 2:
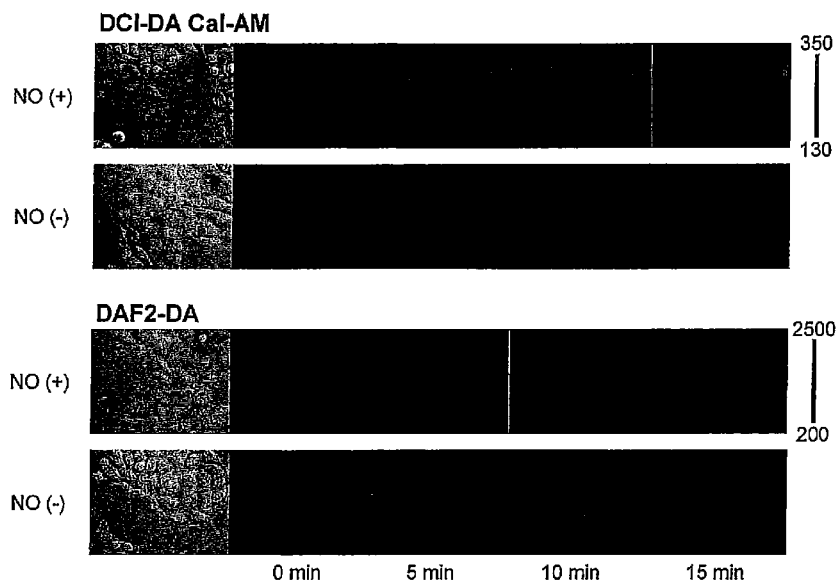
FIG. 2 shows results of imaging with DAF2-DA or DCl-DA Cal-AM after addition of nitrogen monoxide.

DAF2-DA or DCl-DA Cal-AM (10 μM, 0.1% DMSO was used as cosolvent) was loaded on the HeLa cells for 30 minutes. The medium containing the compound was removed, fresh medium (DMEM) was added to the dish, and the dish was set under a microscope. NOC 13 was added at a final concentration of 100 p M, and the cells were photographed every 5 minutes. The results are shown in FIG. 2. When DAF2-DA was used, increase in fluorescence of the background was observed due to leakage of the compound out of the cells, whilst when DCl-DA Cal-AM was added, increase in fluorescence of the background was not observed.

Figure 3:
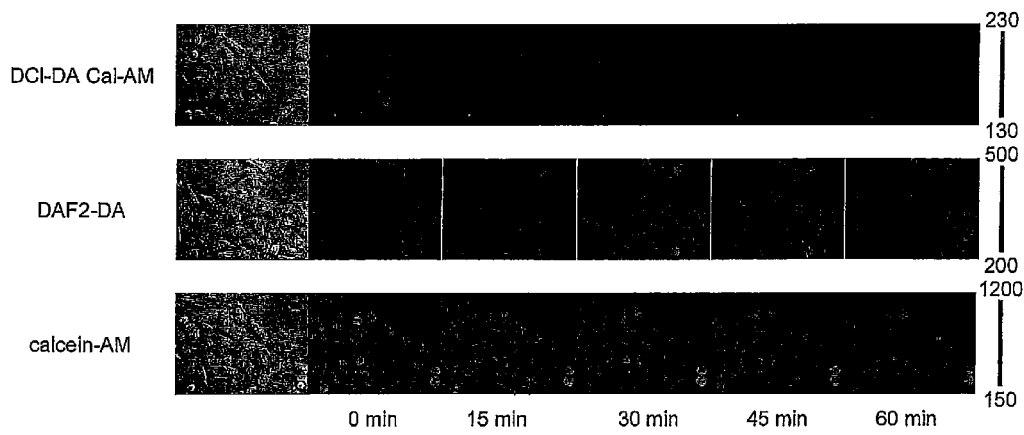
FIG. 3 shows leakage pattern of DAF2-DA or DCl-DA Cal-AM from the inside of cells after addition of nitrogen monoxide.

Leakage from the cells of the triazole compound produced in the cells by the reaction with nitrogen monoxide was observed. In order to confirm that the leakage was not due to damage of cell membranes, calcein-AM (10 μM, 0.1% DMSO was used as cosolvent) was used. DAF2-DA or DCl-DA Cal-AM (10 μM, 0.1% DMSO was used as cosolvent) was loaded on the HeLa cells for 30 minutes. The medium containing the compound was removed, NOC 13 (final concentration: 100 μM) was added to the cells, and the cells were left for 10 minutes and then washed twice. The cells were photographed every 60 minutes, and fluorescence intensity was measured. The results are shown in FIG. 3. When DCl-DA Cal-AM was added, leakage of the fluorescence substance out of the cells was clearly smaller than that observed in the case of adding DAF2-DA.

Figure 4:
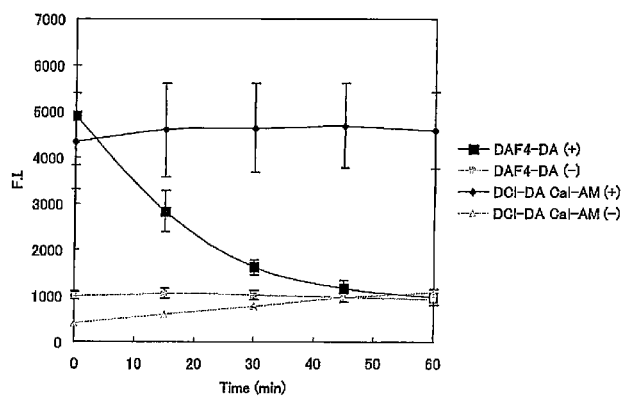
FIG. 4 shows leakage pattern of DAF2-DA or DCl-DA Cal-AM from the inside of cells measured by FACS after addition of nitrogen monoxide.

Then, leakage of the fluorescent substances was compared by using FACS. DAF2-DA or DCl-DA Cal-AM (10 μM, 0.1% DMSO was used as cosolvent) was loaded on the HeLa cells for 30 minutes. The medium containing the compound was removed, NOC 13 (final concentration: 100 μM) was added to the cells, and the cells were left for 20 minutes. The medium containing NOC 13 was removed, and change of the fluorescence intensity was measured by FACS. The results are shown in FIG. 4. These results revealed that the aforementioned triazole compound produced within the cells by addition of DCl-DA Cal-AM gave high intracellular retentivity.

Example 5

It was attempted to visualize a very small amount of NO which is produced actually in cells. It is known that bovine aortic endothelial cells (BAEC) produce NO upon bradykinin stimulus. By using these cells, nitrogen monoxide was imaged with DCl-DA Cal-AM and the conventional fluorescent probe, DAF2-DA.

DAF2-DA or DCl-DA Cal-AM (10 μM, 0.1% DMSO was used as cosolvent) was loaded on the BAEC cells for 60 minutes. The medium containing the compound was removed, and the cells were postincubated for 30 minutes. Fresh medium (HBSS) was added, and observation was started under a microscope (0 second). At the point of 200 seconds, bradykinin was added (final concentration: 0.1 μM), and change of fluorescence was observed (200 to 2000 seconds). In order to confirm that the deesterified compound existed in the cells, NOC 7 was added (final concentration: 100 μM) at the point of 2000 seconds to artificially generate nitrogen monoxide, and change of fluorescence was observed (2000 to 2300 seconds).

Figure 5:
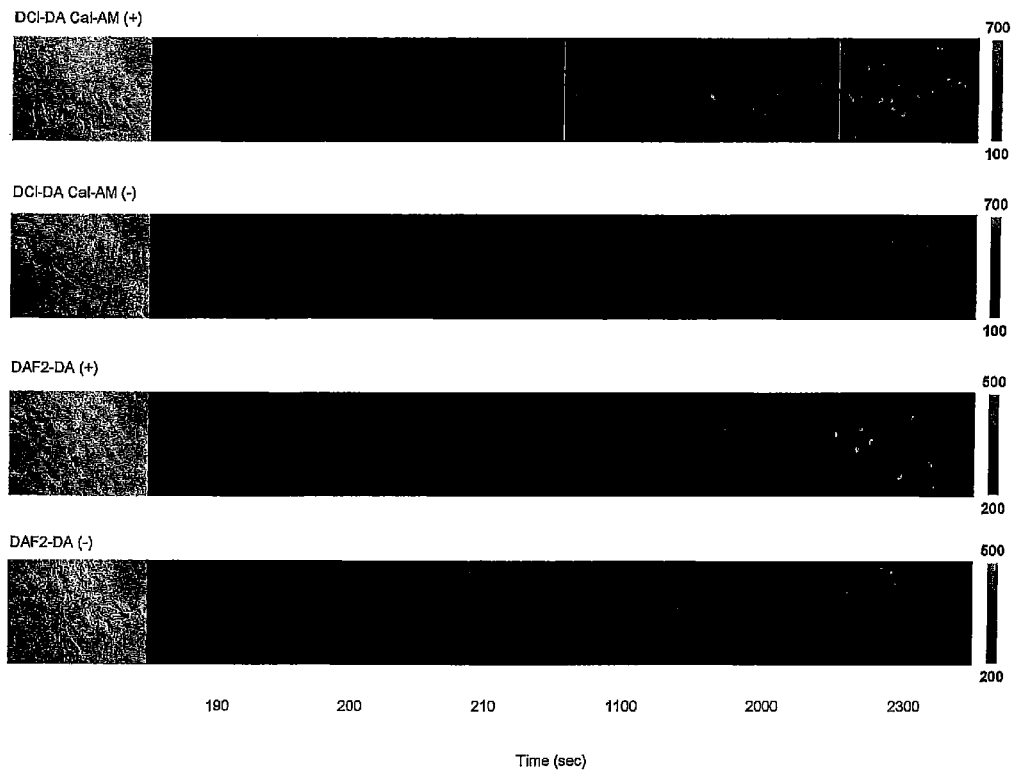
FIG. 5 shows results of imaging of nitrogen monoxide in BAEC cells performed by adding DAF2-DA or DCl-DA Cal-AM.

The results are shown in FIG. 5. Although both DCl-DA Cal-AM and DAF2-DA enabled visualization of nitrogen monoxide produced by the BAEC cells, visualization with DAF2-DA was in such a degree that increase of fluorescence was barely visualized. On the other hand, when DCl-DA Cal-AM was used, distinct increase of fluorescence intensity was observed (refer to, in particular, the result at 2000 seconds). These results indicate that the triazole compound generated from the deesterified compound of DAF2-DA (fluorescence compound) quickly leaks out of the cells, whereas the triazole compound generated from the deesterified compound of DCl-DA Cal-AM (fluorescence compound) is kept in the cells over a long period of time. When NOC 7 was added to artificially generate nitrogen monoxide, elevation of fluorescence intensity was observed in both cases (refer to the results at 2300 seconds).

These results indicate that both DCl-DA Cal-AM and DAF2-DA were sufficiently incorporated into the cells, an extremely small amount of nitrogen monoxide was generated in live cells such as BAEC cells, and only an extremely small part of DCl-DA Cal-AM and DAF2-DA taken up into the cells participated in the detection reaction, and indicate that DCl-DA Cal-AM and the deesterified compound thereof, enabling the imaging without leaking out of the cells over a long period of time, are extremely useful for measuring intracellular nitrogen monoxide over a long period of time.

Figure 6:
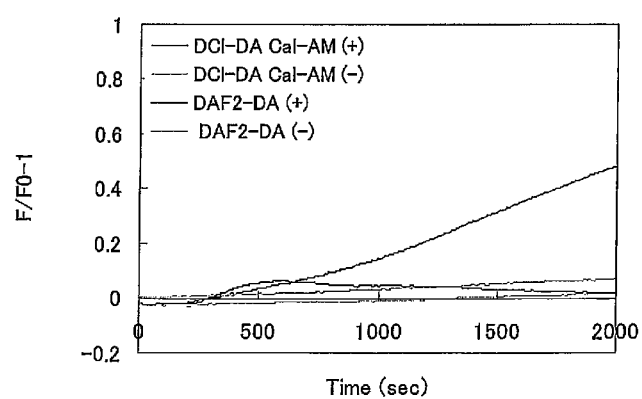
FIG. 6 shows change in average fluorescence intensity indicated in terms of ratio observed from 0 to 2,000 seconds (before addition of NOC7) in the imaging of FIG. 5.

FIG. 6 shows change of average of the fluorescence intensity from 0 to 2000 seconds (before adding NOC7) indicated in terms of ratio. It was confirmed that, with DCl-DA Cal-AM, fluorescence intensity continuously increased with progress of time, whereas, with DAF2-DA, fluorescence intensity decreased from a point after around 600 seconds.

INDUSTRIAL APPLICABILITY

The compounds of the present invention are useful as a reagent for measuring a reactive nitrogen species existing in cells such as nitrogen monoxide or peroxynitrite at high sensitivity over a long period of time.

What is claimed is:

1. A compound or a salt thereof represented by the following formula (A):

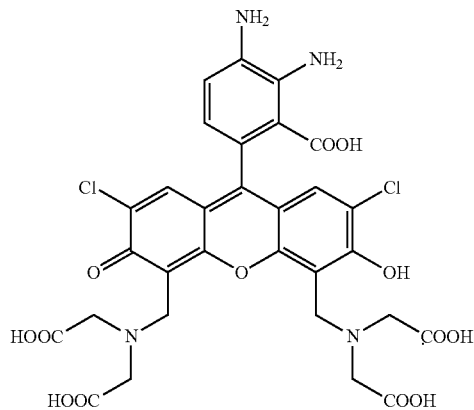

2. A compound represented by the following formula (B):

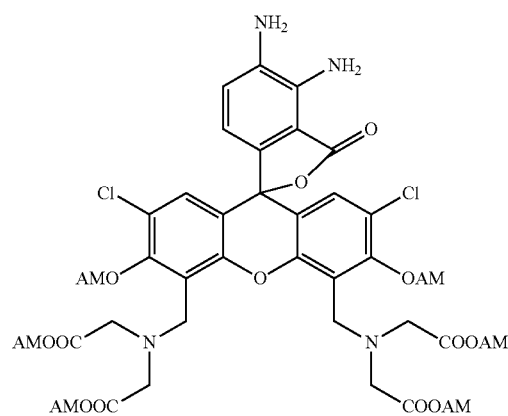

wherein AM is an acetoxymethyl group.

3. A reagent composition for detecting a reactive nitrogen species comprising an additive and as an active ingredient the compound according to claim 2.

4. A method for measuring a reactive nitrogen species, which comprises:
 (1) reacting a compound or a salt thereof represented by the following formula (A):

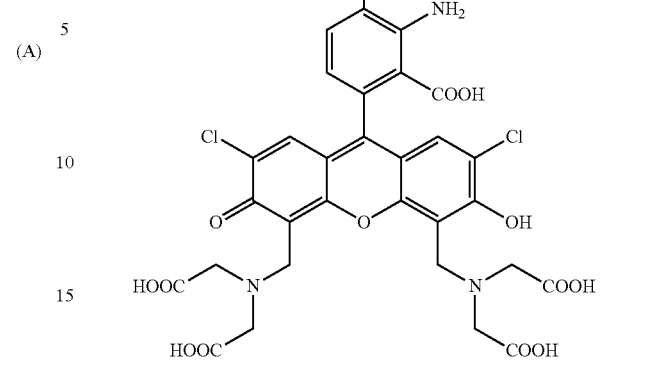

with a reactive nitrogen species to form a fluorescently detectable triazole compound; and
 (2) detecting the fluorescently detectable triazole compound.

5. The method according to claim 4, wherein the reactive nitrogen species is nitrogen monoxide.

6. The method according to claim 4, further comprising uptaking a compound represented by the following formula (B) below into a cell to form the compound or salt thereof represented by formula (A):

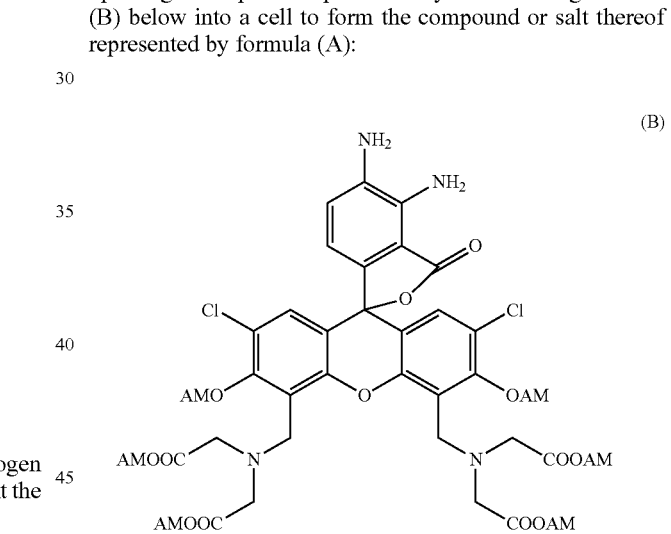

wherein AM is an acetoxymethyl group.

* * * * *